United States Patent [19]

Peake et al.

[11] 4,450,269
[45] May 22, 1984

[54] MONO-5-SUBSTITUTED-3-CHLORO-4H-1,2,6-THIADIAZIN-4-ONE ANTIFUNGAL AGENTS

[75] Inventors: Clinton J. Peake; Wayne N. Harnish, both of Medina; Bruce L. Davidson, Middleport, all of N.Y.

[73] Assignee: FMC Corporation, Philadelphia, Pa.

[21] Appl. No.: 217,644

[22] Filed: Dec. 18, 1980

Related U.S. Application Data

[63] Continuation of Ser. No. 904,828, May 11, 1978, abandoned, which is a continuation of Ser. No. 782,860, Mar. 30, 1977, Pat. No. 4,097,594.

[51] Int. Cl.³ .......................................... C07D 285/16
[52] U.S. Cl. ......................................................... 544/8
[58] Field of Search .............................................. 544/8

[56] References Cited

U.S. PATENT DOCUMENTS 4,201,780   5/1980   Peak et al. ............................... 544/8

OTHER PUBLICATIONS

Geevers et al., Rec. Trav. Chim. vol. 93, pp. 270–272.

*Primary Examiner*—Allen J. Robinson
*Attorney, Agent, or Firm*—Robert L. Andersen; H. Robinson Ertelt

[57] ABSTRACT

Selected mono-5-substituted-3-chloro-4H-1,2,6 thiadiazin-4-ones having the general formula

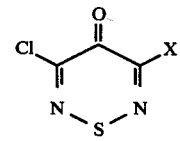

are described which are useful for control of fungal disease in plants.

6 Claims, No Drawings

MONO-5-SUBSTITUTED-3-CHLORO-4H-1,2,6-THIADIAZIN-4-ONE ANTIFUNGAL AGENTS

This application is a continuation of application Ser. No. 904,828 filed May 11, 1978, now abandoned, in turn a division of Ser. No. 782,860, filed Mar. 30, 1977, now U.S. Pat. No. 4,097,594.

BACKGROUND OF THE INVENTION

The present invention relates to a method for controlling fungal disease in plants, to novel antifungal compositions, and to compounds useful for controlling fungi which attack agricultural and garden plants and seeds. More particularly, the invention relates to the use of a selected mono-5-substituted-3-chloro-4H-1,2,6-thiadiazin-4-one as an angifungal agent for controlling fungal disease in plants.

Geevers and Trompen disclosed the preparation 3,5-dichloro-4H-1,2,6-thiadiazin-4-one and its use as an intermediate to prepare various other 5-substituted-3-chloro-4H-1,2,6-thiadiazin-4-ones including the 5-phenoxy derivative. J. Geevers and W. P. Trompen, Rec. Trav. Chim., 93, 270 (1974).

While 5-chloro and 5-phenoxy derivatives and the method for preparing them have been disclosed, the reference provides no indication of any biological activity. More particularly, there is no suggestion that the compounds of this invention have antifungal activity.

It has now been found that selected mono-5-substituted-3-chloro-4H-1,2,6-thiadiazin-4-ones, which are hereinafter described, exhibit excellent antifungal activity and are useful in providing control of fungal disease in agricultural crops by foliar, seed, and soil application.

SUMMARY OF THE INVENTION

The present invention thus provides (1) a method for controlling fungal disease in plants which comprises applying a selected mono-5-substituted-3-chloro-4H-1,2,6-thiadiazin-4-one, as defined below, to the locus where control is desired, (2) antifungal compositions for control of fungal disease in plants, and (3) certain novel compounds which are useful for control of fungi.

DETAILED DESCRIPTION

In accordance with a first aspect of the present invention, there is provided a method for controlling fungal disease in agricultural crops and other plants which comprises applying to the locus where control is desired an effective fungistatic or fungicidal amount of a mono-5-substituted-3-chloro-4H-1,2,6-thiadiazin-4-one of the formula

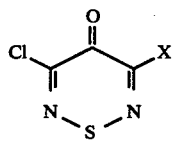
I in which X is halogen, phenoxy, naphthoxy or substituted phenoxy having the formula

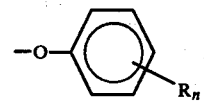
II wherein each R group is a substituent independently selected from lower alkyl, halo, lower alkoxy, hydroxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl, wherein n has a value of 1 to 3 inclusive. However, when each R is halogen n may have a value of 1 to 5 inclusive.

More specifically there is utilized in the method the compounds of formula I in which X is halogen, phenoxy, naphthoxy or substituted phenoxy having the formula II wherein each R group is a substituent independently selected from:

A. lower alkyl, or halo;
B. hydroxy, lower alkoxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl wherein n has a value of 1 to 3 inclusive, except when each R is halogen n has a value of 1 to 5 inclusive, with the proviso that 0 to 2, preferably 0 or 1, R groups may be selected from group B.

Unless it is otherwise indicated, the term "lower" means having 1 to 6 carbon atoms, straight or branched chain, preferably 1 to 4 carbon atoms, and the term "halogen" means bromine, chlorine and fluorine or iodine.

In the method of this invention an effective fungistatic or fungicidal amount of active ingredient is applied to foliage or seeds of agricultural plants or to the soil in which the plants are growing or are to be planted, i.e., the locus where control is desired. When so applied, the compounds prevent fungal infection or inhibit further development of a pre-existing fungal disease.

In the method of this invention the selected antifungal agent may be applied as the technical material, or as a formulated product. Typical formulations include the antifungal agent in combination with an agriculturally acceptable carrier, preferably with a surface active agent, and optionally with other active ingredients. Suitable formulations include granules, powders, or liquids, the choice varying with the fungus and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending on the particular agent used, the additives and carriers used, other active ingredients, and the desired mode of application. With due consideration of these factors, the active ingredient of a typical formulation may, for example, be suitably present at a concentration of about 0.5% up to about 99.5% by weight of the formulation. Additives and carriers may comprise about 99.5% by weight to as low as about 0.5% by weight of the formulation. Surface active agents, if employed in the formulation, may be present at various concentrations, suitably in the range of 1% to 30% by weight.

The formulation may be used as such or diluted to a desired use dilution with a suitable diluent or carrier. The concentration of the active ingredient in use dilution is normally in the range of about 0.001% to about 4% by weight. Many variations of spraying, dusting, soil-incorporated, and controlled or slow release compositions in the art may be used by substituting or adding a compound of this invention into compositions known or apparent to the art.

The antifungal agents of this invention may be formulated and applied with other compatible active ingredients, including nematicides, insecticides, acaricides, other fungicides, plant regulators, herbicides, fertilizers, etc.

In applying the foregoing chemicals, whether alone or with other agricultural chemicals, an effective fungistatic or fungicidal amount of the active ingredient must be applied. While the application rate will vary widely depending on the choice of compound, the formulation and mode of application, the plant species being protected, and the planting density, a suitable use rate may be in the range of 0.05 to 5 kg/hectare, preferably 0.5 to about 4 kg/hectare.

The antifungal composition of this invention comprises a compound of formula I as defined above in admixture with an agriculturally acceptable carrier, preferably containing a compatible surface active agent.

Certain compounds of formula I, notably those in which X is chloro or phenoxy, are disclosed in the cited literature. The novel compounds of this invention are those in which X is other than halogen or phenoxy; that is, the compounds of formula I in which X is naphthoxy or substituted phenoxy having the formula II wherein each R group is a substituent independently selected from lower alkyl, halo, hydroxy, lower alkoxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl wherein n has a value of 1 to 3 inclusive with the proviso that when each R is halogen n may have a value of 1 to 5 inclusive.

More specifically the novel compounds of this invention are those of formula I in which X is naphthoxy or substituted phenoxy having the formula II wherein each R group is a substituent independently selected from:

A. lower alkyl, or halo;
B. hydroxy, lower alkoxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl wherein n has a value of 1 to 3 inclusive, except when each R is halogen n has a value of 1 to 5 inclusive, with the proviso that 0 to 2, preferably 0 or 1, R groups may be selected from group B.

The compounds of this invention are prepared according to the teaching of Geevers and Trompen, supra; that is, by reacting 3,5-dichloro-4H-1,2,6-triadiazin-4-one with alcoholate ions, for example, sodium phenoxide. The following example are typical of the preparation of the compounds.

EXAMPLE I

Synthesis of 3,5-Dichloro-4H-1,2,6-thiadiazin-4-one

A 50 ml flask was charged with 20 ml formic acid. The flask was purged with a stream of dry nitrogen. The nitrogen purge was continued while 6.3 g 3,4,4,5-tetrachloro-4H-1,2,6-thiadiazinone was added dropwise over 0.5 hour during which the temperature of the reaction mixture was maintained at 10±1° C. Following addition the reaction mixture was stirred at 10° C. for 2 hours then at room temperature for 64 hours, then poured into 60 ml. ice-water with stirring. The resulting mixture was filtered and the filter cake washed with water and dried to yield 2.2 g of pale yellow 3,5-dichloro-4H-1,2,6-thiadiazin-4-one, mp 81°–82° C.

EXAMPLE II

Synthesis of 3-Chloro-5-phenoxy-4H-1,2,6-thiadiazin-4-one

A sodium phenoxide solution was prepared by adding 1.0 g of sodium hydroxide to 2.4 g phenol in 25 ml of warm, distilled water. This mixture was stirred for 5 minutes then added to a suspension of 4.6 g of finely ground 3,5-dichloro4H-1,2,6-thiadiazin-4-one in 75 ml of distilled water in a 250 ml flask. This addition required 15 minutes during which the temperature rose to 32° C. After being stirred at room temperature for one hour, the orange mixture was filtered, and the filter cake was washed with water. Recrystallization from 100 ml of ethanol yielded 4.2 g of fluffy, pale yellow needles of 3-chloro-5-phenoxy-4H-1,2,6-thiadiazin-4-one, mp 121°–123° C. (Lit. mp 122.5°–123.5° C., J. Geevers and W. P. Trompen, supra.) An ir spectrum was consistent with the assigned structure.

Analyses calc'd for $C_9H_5ClN_2O_2S$: C 44.92; H 2.09; N 11.64; Found: C 44.94; H 2.26; N 11.63.

The compounds of this invention which are set forth below have been synthesized in accordance with the typical preparatory method set forth in Examples I and II. An identifying number is provided for each compound. This compound number is used below in reporting biological data relating to the compound.

| Compound No. | Identity |
| --- | --- |
| 1 | 3,5-dichloro-4H—1,2,6-thiadiazin-4-one |
| 2 | 3-chloro-5-phenoxy-4H—1,2,6-thiadiazin-4-one |
| 3 | 3-chloro-5-(4-methylphenoxy)-4H—1,2,6-thiadiazin-4-one |
| 4 | 3-chloro-5-(4-tert-butylphnoxy)-4H—1,2,6-thiadiazin-4-one |
| 5 | 3-chloro-5-(4-methoxyphenoxy)4H—1,2,6-thiadiazin-4-one |
| 6 | 3-chloro-5-(4-n-butoxyphenoxy)-4H—1,2,6-thiadiazin-4-one |
| 7 | 3-chloro-5-(4-ethoxycarbonylphenoxy)-4H—1,2,6-thiadiazin-4-one |
| 8 | 5-(4-acetylaminophenoxy)-3-chloro-4H—1,2,6-thiadiazin-4-one |
| 9 | 3-chloro-5-(4-nitrophenoxy)-4H—1,2,6-thiadiazin-4-one |

| Compound No. | Identity |
|---|---|
| 10 | 3-chloro-5-(4-cyanophenoxy)-4H—1,2,6-thiadiazin-4-one |
| 11 | 3-chloro-5-(4-fluorophenoxy)-4H—1,2,6-thiadiazin-4-one |
| 12 | 3-chloro-5-(4-chlorophenoxy)-4H—1,2,6-thiadiazin-4-one |
| 13 | 3-chloro-5-(3-chlorophenoxy)-4H—1,2,6-thiadiazin-4-one |
| 14 | 3-chloro-5-(2-chlorophenoxy)-4H—1,2,6-thiadiazin-4-one |
| 15 | 3-chloro-5-(4-bromophenoxy)-4H—1,2,6-thiadiazin-4-one |
| 16 | 3-chloro-5-(3,4-dichlorophenoxy)-4H—1,2,6-thiadiazin-4-one |
| 17 | 3-chloro-5-(2,4-dichlorophenoxy)-4H—1,2,6-thiadiazin-4-one |
| 18 | 3-chloro-5-(2,6-dichlorophenoxy)-4H—1,2,6-thiadiazin-4-one |
| 19 | 3-chloro-5-(2,3-dichlorophenoxy)-4H—1,2,6-thiadiazin-4-one |
| 20 | 3-chloro-5-(3,5-dichlorophenoxy)-4H—1,2,6-thiadiazin-4-one |
| 21 | 3-chloro-5-(3-methylphenoxy)-4H—1,2,6-thiadiazin-4-one |
| 22 | 3-chloro-5-(2-methylphenoxy)-4H—1,2,6-thiadiazin-4-one |
| 23 | 3-chloro-5-(2,4-dimethylphenoxy)-4H—1,2,6-thiadiazin-4-one |
| 24 | 3-chloro-5-(2,6-dimethylphenoxy)-4H—1,2,6-thiadiazin-4-one |
| 25 | 3-chloro-5-(3,5-dimethylphenoxy)-4H—1,2,6-thiadiazin-4-one |
| 26 | 5-(4-aminophenoxy)-3-chloro-4H—1,2,6-thiadiazin-4-one |
| 27 | 5-(4-aminophenoxy)-3-chloro-4H—1,2,6-thiadiazine-4-one hydrochloride |
| 28 | 3-chloro-5-[4-(3-methylureido)-phenoxy]-4H—1,2,6-thiadiazin-4-one |
| 29 | 3-chloro-5-[4-(3-phenylureido)-phenoxy]-4H—1,2,6-thiadiazin-4-one |
| 30 | 3-chloro-5-(2,4,6-trichlorophenoxy)-4H—1,2,6-thiadiazin-4-one |
| 31 | 3-chloro-5-(pentachlorophenoxy)-4H—1,2,6-thiadiazine-4-one |
| 32 | 3-chloro-5(1-naphthoxy)-4H-1,2,6-thiadiazin-4-one |
| 33 | 3-chloro-5-(bromophenoxy)-4H-1,2,6-thiadiazin-4-one |
| 34 | 3-chloro-5-(2-bromophenoxy)-4H-1,2,6,-thiadiazin-4-one |
| 35 | 3-chloro-5-(4-hydroxyphenoxy)-4H-1,2,6-thiadiazin-4-one |
| 36 | 3-chloro-5-[methylaminocarbonyloxy)phenoxy]-4H-1,2,6-thiadiazin-4-one |
| 37 | 3-chloro-5-[4-(phenylaminocarbonyloxy)phenoxy]-4H-1,2,6,-thiadiazin-4-one |
| 38 | 3-chloro-5-[4-(phenyl methoxycarbonyloxy)phenoxy]-4H-1,2,6-thiadiazin-4-one |
| 39 | 3-chloro-5-[(4-methyl-thio)phenoxy]-4H-1,2,6,-thiadiazin-4-one |
| 40 | 3-chloro-5-[(4-methyl-sulfinyl)phenoxy]-4H-1,2,6,-thiadiazin-4-one |
| 41 | 3-chloro-5-[(4-methyl-sulfonyl)phenoxy]-4H—1,2,6-thiadiazin-4-one |
| 42 | 3-[(3-N—acetylamino)-phenoxy]-5-chloro-4H—1,2,6-thiadiazin-4-one |
| 43 | 3-[(2-acetylamino)-phenoxy]-5-chloro-4H—1,2,6-thiadiazin-4-one |
| 44 | 3-chloro-5-[(3-trifluoromethyl)phenoxy]-4H—1,2,6-thiadiazin-4-one |
| 45 | 3-(2-carboxymethylphenoxy)-5-chloro-4H—1,2,6-thiadiazin-4-one |
| 46 | 3-chloro-5-[(4-cyanomethyl)phenoxy]4H—1,2,6-thiadiazin-4-one |
| 47 | 3-(4-acetylphenoxy)-5-chloro-4H—1,2,6-thiadiazin-4-one |
| 48 | 3-(3-acetylphenoxy)-5-chloro-4H—1,2,6-thiadiazin-4-one |
| 49 | 3-(2-acetylphenoxy)-5-chloro-4H—1,2,6-thiadiazin-4-one |
| 50 | 3-(4-carboxyphenoxy)-5-chloro-4H—1,2,6-thiadiazin-4-one |
| 51 | 3-chloro-5-[(2-chloro-5-methoxy)phenoxy]-4H—1,2,6-thiadiazin-4-one |
| 52 | 3-chloro-5-[(3-chloro-5-methoxy)phenoxy]-4H—1,2,6-thiadiazin-4-one |
| 53 | 3-chloro-5-(2-chloro-4-nitrophenoxy)-4H—1,2,6-thiadiazin-4-one |
| 54 | 3-chloro-5-(4-chloro-3-methylphenoxy)-4H—1,2,6-thiadiazin-4-one |
| 55 | 3-chloro-5-(4-chloro-2-methylphenoxy)-4H—1,2,6-thiadiazin-4-one |
| 56 | 3-chloro-5-[(2-chloro-5-methyl)phenoxy]-4H—1,2,6-thiadiazin-4-one |
| 57 | 3-[(2-bromo-4-methyl)-phenoxy]-5-chloro-4H—1,2,6-thiadiazin-4-one |
| 58 | 3-chloro-5-[(2-chloro-4,5-dimethyl)phenoxy]-4H—1,2,6-thiadiazin-4-one |
| 59 | 3-chloro-5-[(4-chloro-3,5-dimethyl)phenoxy]-4H—1,2,6-thiadiazin-4-one |
| 60 | 3-[(4-bromo-3,5-dimethyl)-phenoxy]-5-chloro-4H—1,2,6-thiadiazin-4-one |
| 61 | 3-[(4-acetyl-3,5-dimethoxy)-phenoxy]-5-chloro-4H—1,2,6-thiadiazin-4-one |

The following examples demonstrate the practice of the present invention. The test organisms used in these examples, together with an identifying code which are in the tables to identify each organism, are as follows:

| | |
|---|---|
| AS = *Alternaria solani* | PO = *Pyricularia oryzae* |
| BC = *Botrytis cinerea* | PU = *Pythium ultimum* |
| CC = *Cladosporium cucumerinum* | RS = *Rhizoctonia solani* |
| EP = *Erysiphe polygoni* | SF = *Sclerotinia fructicola* |
| PS = *Fusarium solani* | UP = *Uromyces phaseoli* |
| HO = *Helminthosporium oryzae* | VI = *Venturia inaequalis* |
| PI = *Phytophthora infestans* | |

EXAMPLE III

Spore Germination Tests

The test chemical was dissolved or suspended in acetone in an amount such that 0.8 ml of the resulting suspension or solution, mixed with 40 ml water agar produced a water agar solution containing 40, 10, 2.5 and 1 ppm of test chemical. The resulting agar solution, at 50° C., was then divided equally between two sterile petri dishes, each having four separated quadrants, and allowed to solidify. Three quadrants of each dish were flooded with 0.1 ml of a spore suspension in sterile water. Spores of two pathogens, *Erysiphe polygoni* and *Uromyes phaseoli*, from infected plant leaves, were brushed on the remaining two quadrants. The tests were then incubated 48 hours, at 24° C.

Readings were then taken and the percentage of germinated spores calculated. From this percentage, a spore germination rating was assigned as follows:

| Germination | Rating |
|---|---|
| 0–10 | 0 |
| 10–40 | 1 |
| 40–60 | 2 |
| 60–80 | 3 |
| 80–100 | 4 |

Table I reports the inhibitory effect of these test compounds on spore germination and demonstrates improvement over benomyl which was used as a standard for comparison. In Table I, the lower the numeral used as a rating, the more effective the compound.

EXAMPLE IV

Mycelial Growth Tests

Aliquots of previously prepared solutions of active ingredient in acetone were added to tubes containing 20 ml of sterile, melted potato dextrose agar that had been cooled to 50° C. to provide mixtures of 40, 20, 10, 5 and 2.5 ppm. The tubes were shaken to ensure thorough mixing of the chemical with the agar, and the mixture poured into petri dishes having 4 quadrants to solidify. Each quadrant was inoculated with a 4 mm diameter disc of agar containing mycelium of the test fungi and incubated at 25° C. for 72 hours during which the samples were alternately exposed to light for 12 hours and to darkness for 12 hours. Growth was measured at the end of the incubation period by measuring the diameter of each fungus colony. Two measurements of the diameter, perpendicular to each other, were taken and the values averaged. Data are reported as percent inhibition (%I) by the following formula:

$$\% I = \frac{\text{mm growth of check} - \text{mm growth of treated sample}}{\text{mm growth of check}}$$

Captan and chlorothalonil were used as standards for comparison. The results reported in Table II indicate that the test compounds were generally more active than the standards.

EXAMPLE V

The compounds of this invention were tested for crop disease control to determine the basic types of antifungal activity they exhibit.

A. Foliar Protective Activity

The foliage of a tomato plant in the four leaf stage and a pinto bean in the primary leaf stage was sprayed with the test chemicals at a concentrations of 150 ppm on a weight/volume basis, and the plant allowed to dry overnight.

Sporangia of *Phytophthora infestans* (late blight fungus) were harvested from cultures grown on lima bean agar for 10 to 14 days. A water suspension of sporangia ($2 \times 10^5$ sporangia/ml) was incubated at 12° C. for two hours in order to provide a zoospore suspension. Spores of *Uromyces phaseoli* (bean rust fungus) were collected from diseased plants and a 2% spore powder mixture prepared using ABB Pyrax talc as a diluent.

The tomato plants were inoculated in a spray hood with the zoospore suspension, then immediately incubated in a humidity chamber at 100% relative humidity at 18°–20° C. for four to five days. The bean plants were inoculated by dusting the spore powder onto the leaves. This was accomplished by placing the spore powder in a cheesecloth bag and shaking the bag over the leaves. The inoculated plants were placed in the humidity chamber at 100% relative humidity and 21° C. for 24 hours and then placed in the greenhouse for four to six days until disease symptoms developed.

The percent disease control was then determined by comparing the disease incidence in treated plants and untreated check plants. Results reported in Table III demonstrate the efficacy of the compounds tested in preventing tomato late blight and bean rust when applied to foliage of uninfected plants at 150 ppm prior to disease infestation.

B. Foliar Curative Tests

In the curative tests the plants were inoculated with the appropriate pathogen 24 hours before chemical treatment. The following host-parasite combinations were used:

| PLANT | FUNGUS | DISEASE |
|---|---|---|
| *Phaseolus vulgaris* L. | *Uromyces phaseoli* Link | bean rust |
| *Phaseolus vulgaris* L. | *Erysiphe polygoni* DC | bean powdery mildew |
| *Beta vulgaris* | *Cercospora beticola* | sugar beet leaf spot |
| *Oryzae sativa* L. | *Pyricularia oryzae* | rice blast |

Spores of bean rust and bean powdery mildew were obtained from diseased plants. Spores of *Cercospora beticola* and *Pyricularia oryzae* were harvested from petri dish cultures. *C. beticola* was grown on potato dextrose agar and *P. oryzae* on a glucose yeast extract medium. The cultures were grown at 25° C. for 10 days.

Beans (c.v. 'Pinto') were inoculated with rust as described in Example IV-A. Beans (c.v. 'Bountiful') at primary leaf stage were inoculated with powdery mildew by shaking diseased leaves over the test plants, thereby creating a spore deposit on leaves of the test plants. Sugar beets and rice were inoculated by spraying a water suspension of spores of the appropriate pathogen on the foliage.

All of the plants except those inoculated with bean powdery mildew were incubated in the moisture chamber (21° C.) for 24 hours. The bean powdery mildew inoculated plants were incubated in the greenhouse.

The test chemical was sprayed on the foliage of the plants at 150 ppm 24 hours after inoculation. The bean and rice plants were removed from the moisture chamber and allowed to dry before chemical treatment. After treatment the plants were incubated in the greenhouse for 6–10 days. The sugar beets were sprayed while still wet, after which they were immediately returned to the moisture chamber for two days and then to the greenhouse for 10–14 days.

The results tabulated in Table III demonstrate curative activity when applied after infection of the plant.

C. Soil/Seed Treatment

Containers having a volume of about 0.25 l. were ⅔ filled with topsoil and 25 cucumber c.v. [Straight Eight' seeds deposited on the soil surface of each pot. A suspension containing 150 ppm of the test chemical was poured over the seeds and into the soil in sufficient quantity to provide 3.75 to 3.8 mg active ingredient per pot.

Fungi used in this test were *Pythium ultimum* and *Rhizoctonia solani*. These fungi were each grown on potato dextrose agar for three to six days. The agar plus mycelium was then minced in a blender with water and 10 ml of the resulting slurry of minced mycelium poured over the seeds.

Following inoculation approximately 15 mm of topsoil was spread over the seeds, the container capped and incubated at 4° C. in darkness for three days, then transferred to a greenhouse (27° C.) for 10–14 days, at which time stand counts were made. Captan was used as a standard for comparison. Based on stand counts on Efficacy Index was calculated for each test chemical as follows:

$$\text{Efficacy Index} = \frac{\text{Test Stand} - \text{Untreated Stand}}{\text{Captan Stand} - \text{Untreated Stand}} \times 100$$

The results, set forth in Table III, show that many of the compounds tested were considerably more effective than captan for treatment of Cucumber damping-off complex.

In a similar manner the soil around a bean seedling was drenched with a sufficient amount of 150 ppm suspension of test chemical to provide 3.8 mg active per pot. Twenty-four hours later the soil was inoculated with a suspension of minced mycelium of *Fusarium solani*. The inoculated plants were then placed in a greenhouse, evaluated after fourteen days, and percent control of root rot damage calculated. The results, reported in Table III, indicate only a few of the compounds tested are effective in treating Bean Root Rot but that these provide a high degree of control.

TABLE I
RESULTS OF IN VITRO SPORE GERMINATION INHIBITION TESTING

| CPD No. | Conc. ppm | BC | PO | VI | AS | CC | PI | EP | UP |
|---|---|---|---|---|---|---|---|---|---|
| 2 | 40 | 0 | 0 | 0 | 0 | 0 | 0 | 1 | 0 |
|   | 10 | 0 | 0 | 0 | 0 | 0 | 1 | 3 | 0 |
|   | 2.5 | 4 | 1* | 2* | 0 | 4 | 1 | 4 | 2 |
|   | 1.0 | 4 | 3 | 4 | 4 | 4 | 0 | 4 | 2 |
| 3 | 40 | 0 | 0 | 0 | 0 | 0 | 0 | 1 | 0 |
|   | 10 | 0 | 0 | 0 | 0 | 0 | 0 | 4 | 0 |
|   | 2.5 | 4 | 4 | 4* | 4 | 4 | 2 | 4 | 1* |
|   | 1.0 | 4 | 0 | 4 | 4 | 4 | 3 | 4 | 4 |
| 4 | 40 | 2* | 0 | 0 | 4 | 0 | 0 | 0 | 0 |
|   | 10 | 4 | 0 | 0 | 4 | 0 | 0 | 2 | 0 |
|   | 2.5 | 4 | 4 | 4 | 4 | 4 | 3 | 3 | 4 |
|   | 1.0 | 4 | 4 | 4 | 4 | 4 | 4 | 4 | 4 |
| 5 | 40 | 0 | 0 | 0 | 0 | 0 | 0 | 0 | 0 |
|   | 10 | 1* | 0 | 0 | 0 | 0 | 2 | 4 | 0 |
|   | 2.5 | 4 | 1* | 0 | 0 | 4 | 2 | 4 | 1 |
|   | 1.0 | 4 | 4 | 3* | 2 | 4 | 2 | 4 | 1 |
| 6 | 40 | 4 | 0 | 0 | 4 | 0 | 0 | 0 | 0 |
|   | 10 | 4 | 2* | 0 | 4 | 0 | 0 | 0 | 0 |
|   | 2.5 | 4 | 1* | 0 | 4 | 0 | 0 | 0 | 0 |
|   | 1.0 | 4 | 2* | 1 | 4 | 0 | 2 | 0 | 1 |
| 7 | 40 | 3 | 1* | 0 | 4 | 1 | 0 | 0 | 0 |
|   | 10 | 2 | 1* | 0 | 4 | 0 | 0 | 2 | 0 |
|   | 2.5 | 3 | 1* | 0 | 4 | 0 | 0 | 3 | 0 |
|   | 1.0 | 4 | 1 | 0 | 4 | 0 | 0 | 4 | 0 |
| 8 | 40 | 4 | 0 | 0 | 0 | 0 | 0 | 2 | 0 |
|   | 10 | 4 | 0 | 2* | 2 | 0 | 0 | 4 | 0 |
|   | 2.5 | 4 | 3 | 3 | 2 | 3 | 4 | 4 | 4 |
|   | 1.0 | 4 | 4 | 4 | 3 | 4 | 4 | 4 | 4 |
| 9 | 40 | 0 | 0 | 0 | 0 | 0 | 0 | 4 | 0 |
|   | 10 | 0 | 0 | 0 | 0 | 0 | 0 | 4 | 0 |
|   | 2.5 | 0 | 0 | 0 | 0 | 0 | 0 | 4 | 0 |
|   | 1.0 | 0 | 0 | 0 | 0 | 0 | 0 | 4 | 0 |
| 10 | 40 | 0 | 0 | 0 | 1 | 0 | 1 | 1 | 0 |
|    | 10 | 0 | 0 | 0 | 1 | 0 | 0 | 2 | 0 |
|    | 2.5 | 0 | 0 | 0 | 1 | 0 | 0 | 2 | 0 |
|    | 1.0 | 2 | 0 | 0 | 1 | 0 | 0 | 2 | 0 |
| 11 | 40 | 0 | 0 | 0 | 0 | 0 | 0 | 0 | 0 |
|    | 10 | 0 | 0 | 0 | 0 | 0 | 0 | 0 | 0 |
|    | 2.5 | 1 | 0 | 1 | 0 | 0 | 0 | 0 | 0 |
|    | 1.0 | 4 | 3 | 4 | 4 | 0 | 4 | 0 | 4 |
| 12 | 40 | 0 | 0 | 0 | 0 | 0 | 0 | 0 | 0 |
|    | 10 | 0 | 0 | 1* | 0 | 0 | 1 | 2 | 0 |
|    | 2.5 | 2 | 0 | 1* | 0 | 0 | 1 | 4 | 1 |
|    | 1.0 | 0 | 0 | 1 | 3 | 2 | 1 | 4 | 1 |
| 13 | 40 | 0 | 0 | 0 | 0 | 0 | 0 | 0 | 0 |
|    | 10 | 0 | 0 | 0 | 0 | 0 | 0 | 0 | 0 |
|    | 2.5 | 4 | 0 | 0 | 0 | 0 | 0 | 2 | 0 |
|    | 1.0 | 4 | 3 | 1* | 2 | 2 | 0 | 4 | 0 |
| 14 | 40 | 0 | 0 | 0 | 0 | 0 | 0 | 0 | 0 |
|    | 10 | 0 | 0 | 0 | 0 | 0 | 0 | 2 | 0 |
|    | 2.5 | 0 | 0 | 0 | 2* | 0 | 0 | 4 | 0 |
|    | 1.0 | 3 | 3 | 0 | 3 | 4 | 0 | 4 | 0 |
| 15 | 40 | 0 | 0 | 0 | 0 | 0 | 0 | 0 | 0 |
|    | 10 | 0 | 0 | 0 | 0 | 0 | 0 | 0 | 0 |
|    | 2.5 | 1 | 1 | 0 | 1 | 0 | 1 | 1 | 0 |
|    | 1.0 | 4 | 0 | 0 | 4 | 0 | 0 | 4 | 1 |
| 16 | 40 | 1* | 0 | 0 | 0 | 0 | 0 | 4 | 0 |
|    | 10 | 0 | 0 | 0 | 0 | 0 | 0 | 1 | 0 |
|    | 2.5 | 1* | 0 | 0 | 0 | 0 | 0 | 3 | 0 |
|    | 1.0 | 4 | 0 | 0 | 1 | 0 | 1 | 4 | 1 |
| 17 | 40 | 0 | 0 | 0 | 0 | 0 | 0 | 0 | 0 |
|    | 10 | 0 | 0 | 0 | 0 | 0 | 0 | 0 | 0 |
|    | 2.5 | 0 | 0 | 0 | 1 | 0 | 0 | 1 | 0 |
|    | 1.0 | 4 | 0 | 0 | 2* | 4 | 3 | 3 | 0 |
| 18 | 40 | 0 | 0 | 0 | 0 | 0 | 0 | 0 | 0 |
|    | 10 | 0 | 0 | 0 | 1* | 0 | 0 | 0 | 0 |
|    | 2.5 | 1* | 2 | 0 | 2* | 0 | 0 | 1 | 0 |
|    | 1.0 | 4 | 4 | 1 | 3 | 4 | 3 | 2 | 0 |
| 19 | 40 | 0 | 0 | 0 | 0 | 0 | 0 | 0 | 0 |
|    | 10 | 0 | 0 | 0 | 0 | 0 | 0 | 0 | 0 |
|    | 2.5 | 1 | 0 | 0 | 3 | 0 | 0 | 1 | 0 |
|    | 1.0 | 4 | 3 | 1* | 3 | 2 | 3 | 3 | 0 |
| 20 | 40 | 0 | 0 | 0 | 0 | 0 | 0 | 0 | 0 |
|    | 10 | 0 | 0 | 0 | 0 | 0 | 0 | 0 | 0 |
|    | 2.5 | 0 | 0 | 0 | 0 | 0 | 0 | 0 | 0 |
|    | 1.0 | 4 | 1 | 0 | 2 | 0 | 0 | 3 | 0 |
| 21 | 40 | 0 | 0 | 0 | 0 | 0 | 0 | 0 | 0 |
|    | 10 | 0 | 0 | 0 | 0 | 0 | 0 | 2 | 0 |
|    | 2.5 | 3 | 0 | 3 | 1* | 0 | 1 | 3 | 2 |
|    | 1.0 | 4 | 4* | 4 | 3 | 1 | 4 | 4 | 4 |
| 22 | 40 | 0 | 0 | 0 | 0 | 0 | 0 | 1 | 0 |
|    | 10 | 0 | 0 | 0 | 0 | 0 | 0 | 3 | 1 |
|    | 2.5 | 0 | 0 | 0 | 0 | 0 | 0 | 4 | 2 |
|    | 1.0 | 2 | 2 | 0 | 3 | 0 | 0 | 4 | 4 |
| 23 | 40 | 0 | 0 | 0 | 0 | 0 | 0 | 1 | 0 |
|    | 10 | 4* | 0 | 1 | 0 | 0 | 2 | 3 | 1 |
|    | 2.5 | 4* | 0 | 3 | 3 | 1 | 2 | 4 | 4 |
|    | 1.0 | 4 | 4 | 4 | 3 | 4 | 4 | 4 | 4 |
| 24 | 40 | 0 | 0 | 0 | 0 | 0 | 0 | 0 | 0 |
|    | 10 | 0 | 0 | 0 | 0 | 0 | 1 | 0 | 0 |
|    | 2.5 | 1 | 0 | 0 | 1* | 0 | 2 | 1 | 0 |
|    | 1.0 | 3 | 3 | 2 | 1 | 0 | 4 | 3 | 1 |
| 25 | 40 | 0 | 0 | 0 | 0 | 0 | 0 | 0 | 0 |
|    | 10 | 0 | 0 | 2 | 0 | 0 | 0 | 0 | 1 |
|    | 2.5 | 1* | 0 | 0 | 2 | 0 | 1 | 4 | 2 |
|    | 1.0 | 2 | 3 | 4 | 4 | 0 | 4 | 4 | 4 |
| 26 | 40 | 0 | 0 | 1 | 0 | 0 | 2* | 4 | 2 |
|    | 10 | 0 | 0 | 4 | 0 | 0 | 4 | 4 | 4 |
|    | 2.5 | 0 | 2* | 4 | 3 | 0 | 4 | 4 | 3 |
|    | 1.0 | 0 | 4 | 4 | 4 | 1 | 4 | 4 | 2 |
| 27 | 40 | 0 | 0 | 0 | 0 | 0 | 2 | 4 | 0 |
|    | 10 | 0 | 0 | 0 | 3* | 0 | 4 | 4 | 1 |

TABLE I-continued
RESULTS OF IN VITRO SPORE GERMINATION INHIBITION TESTING

| CPD No. | Conc. ppm | BC | PO | VI | AS | CC | PI | EP | UP |
|---|---|---|---|---|---|---|---|---|---|
|  | 2.5 | 0 | 0 | 0 | 4 | 0 | 3 | 4 | 1 |
|  | 1.0 | 1* | 4 | 0 | 4 | 1 | 4 | 4 | 4 |
| 28 | 40 | 0 | 1 | 3 | 4 | 0 | 2 | 4 | 2 |
|  | 10 | 0 | 4 | 2 | 4 | 1 | 4 | 4 | 2 |
|  | 2.5 | 1 | 4 | 4 | 4 | 2 | 4 | 4 | 2 |
|  | 1.0 | 4 | 4 | 4 | 4 | 2 | 4 | 4 | 4 |
| 29 | 40 | 2* | 2* | 0 | 4 | 1 | 3 | 1 | 0 |
|  | 10 | 2* | 4 | 4 | 4 | 2 | 4 | 4 | 2 |
|  | 2.5 | 3 | 4 | 4 | 4 | 2 | 4 | 4 | 2 |
|  | 1.0 | 3 | 4 | 4 | 4 | 2 | 4 | 4 | 4 |
| 30 | 40 | 0 | 0 | 0 | 0 | 0 | 0 | 0 | 0 |
|  | 10 | 0 | 0 | 0 | 0 | 0 | 0 | 0 | 0 |
|  | 2.5 | 0 | 0 | 0 | 0 | 0 | 1 | 0 | 0 |
|  | 1.0 | 0 | 3 | 1 | 3 | 0 | 4 | 1 | 0 |
| 31 | 40 | 0 | 0 | 0 | 0 | 0 | 2 | 0 | 0 |
|  | 10 | 1* | 0 | 0 | 0 | 0 | 2 | 1 | 0 |
|  | 2.5 | 1* | 0 | 0 | 1 | 0 | 3 | 0 | 0 |
|  | 1.0 | 1* | 0 | 0 | 4 | 0 | 4 | 0 | 0 |
| 32 | 40 | 0 | 0 | 0 | 0 | 0 | 0 | 0 | 0 |
|  | 10 | 0 | 0 | 0 | 0 | 0 | 0 | 0 | 0 |
|  | 2.5 | 0 | 0 | 0 | 1 | 0 | 1 | 2 | 0 |
|  | 1.0 | 2 | 2 | 3 | 3 | 0 | 3 | 2 | 3 |
| 33 | 40 | 0 | 0 | 0 | 0 | 0 | 0 | 0 | 0 |
|  | 10 | 0 | 0 | 0 | 0 | 0 | 0 | 0 | 0 |
|  | 2.5 | 3 | 0 | 0 | 0 | 0 | 0 | 0 | 0 |
|  | 1.0 | 4 | 2* | 0 | 1* | 0 | 0 | 0 | 0 |
| 34 | 40 | 0 | 0 | 0 | 0 | 0 | 0 | 0 | 0 |
|  | 10 | 0 | 0 | 0 | 0 | 0 | 0 | 0 | 0 |
|  | 2.5 | 0 | 0 | 0 | 1* | 0 | 1 | 2 | 0 |
|  | 1.0 | 2* | 1* | 0 | 4* | 1* | 4 | 0 | 0 |
| 35 | 40 | 3* | 0 | — | 0 | 0 | 0 | 1 | 0 |
|  | 10 | 4 | 0 | — | 3* | 3* | 0 | 2 | 0 |
|  | 2.5 | 4 | 0 | — | 4* | 0 | 4 | 0 | 0 |
|  | 1.0 | 4 | 2 | — | 4 | 4 | 4 | 4 | 0 |
| 36 | 40 | 2 | 0 | — | 0 | 0 | 0 | 1* | 0 |
|  | 10 | 4 | 0 | — | 2* | — | 4 | 1* | 0 |
|  | 2.5 | 4 | 2* | — | 4 | 3* | 4 | 3* | 2 |
|  | 1.0 | 4 | 4 | — | 4 | 4 | 4 | 4* | 4 |
| 37 | 40 | 4 | 2 | — | 3 | 0 | 4 | 3 | 1 |
|  | 10 | 4 | 0 | — | 4 | 0 | 4 | 4 | 1 |
|  | 2.5 | 4 | 3 | — | 4 | 1* | 4 | 4 | 2 |
|  | 1.0 | 4 | 4 | — | 4 | 0 | 4 | 4 | 4 |
| 38 | 40 | 3 | 2 | — | 4 | 3 | 3 | 4 | 2* |
|  | 10 | 4 | 2 | — | 4 | 3 | 4 | 4 | 3 |
|  | 2.5 | 4 | 3 | — | 4 | 4 | 4 | 4 | 4 |
|  | 1.0 | 4 | 4 | — | 4 | 4 | 4 | 4 | 4 |
| 39 | 40 | 3 | 0 | — | 0 | 0 | 3 | 0 | 0 |
|  | 10 | 4 | 1 | — | 2 | 0 | 3 | 2 | 2 |
|  | 2.5 | 4 | 1 | — | 3 | 0 | 4 | 1 | 2 |
|  | 1.0 | 4 | 2 | — | 4 | 1 | 4 | 2 | 2 |
| 40 | 40 | 3 | 1 | — | 0 | 0 | 0 | 1 | 1 |
|  | 10 | 4 | 4 | — | 1 | 0 | 2 | 4 | 1 |
|  | 2.5 | 4 | 3 | — | 2 | 0 | 3 | 4 | 2 |
|  | 1.0 | 4 | 4 | — | 4 | 4 | 4 | 4 | 3 |
| 41 | 40 | 3 | 0 | — | 0 | 0 | 0 | 0 | 0 |
|  | 10 | 4 | 0 | — | 0 | 0 | 0 | 1 | 0 |
|  | 2.5 | 0 | 3 | — | 2 | 0 | 2* | 2 | 1 |
|  | 1.0 | 0 | 4 | — | 4 | 0 | 4 | 2 | 4 |
| 42 | 40 | 1* | 0 | 1 | 2* | 0 | 0 | 4 | 0 |
|  | 10 | 4 | 3 | 4* | 4 | 3 | 3 | 4 | 1 |
|  | 2.5 | 4 | 4 | 4* | 4 | 4 | 4 | 4 | 3 |
|  | 1.0 | 4 | 4 | 4 | 4 | 4 | 4 | 4 | 4 |
| 43 | 40 | 3 | 1 | 2 | 3 | 0 | 2 | 1 | 4 |
|  | 10 | 4 | 4 | 4 | 4 | 2 | 4 | 4 | 4 |
|  | 2.5 | 4 | 4 | 4 | 4 | 4 | 4 | 4 | 4 |
|  | 1.0 | 4 | 4 | 4 | 4 | 4 | 4 | 4 | 4 |
| 44 | 40 | 0 | 0 | 0 | 0 | 0 | 0 | 0 | 0 |
|  | 10 | 0 | 0 | 0 | 0 | 0 | 0 | 0 | 0 |
|  | 2.5 | 3* | 0 | 1* | 1* | 0 | 0 | 1 | 0 |
|  | 1.0 | 4 | 1 | 1* | 4 | 1* | 2 | 3 | 1* |
| 45 | 40 | 2* | 1* | 0 | 2* | 0 | 0 | 2 | 2 |
|  | 10 | 4 | 4 | 4 | 4 | 2 | 0 | 4 | 4 |
|  | 2.5 | 4 | 4 | 4 | 4 | 4 | 4 | 4 | 4 |
|  | 1.0 | 4 | 4 | 4 | 4 | 4 | 4 | 4 | 4 |
| 46 | 40 | 0 | 0 | — | 0 | 0 | 0 | 4 | 0 |
|  | 10 | 3* | 0 | — | 2* | 0 | 1* | 4 | 0 |
|  | 2.5 | 3* | 0 | — | 2* | 0 | 1* | 4 | 0 |
|  | 1.0 | 4 | 0 | — | 4 | 4 | 4 | 4 | 1 |
| 47 | 40 | 0 | 0 | 0 | 0 | 0 | 0 | 1 | 0 |
|  | 10 | 0 | 0 | 0 | 0 | 0 | 0 | 4 | 0 |
|  | 2.5 | 1 | 0 | 0 | 0 | 0 | 0 | 4 | 0 |
|  | 1.0 | 4 | 1 | 1* | 2 | 0 | 0 | 4 | 0 |
| 48 | 40 | 0 | 0 | 0 | 0 | 0 | 0 | 2 | 0 |
|  | 10 | 0 | 0 | 0 | 0 | 0 | 0 | 2 | 0 |
|  | 2.5 | 4 | 1* | 1* | 3 | 0 | 0 | 4 | 0 |
|  | 1.0 | 4 | 3* | 3* | 4 | 0 | 4 | 0 | |
| 49 | 40 | 0 | 0 | 0 | 0 | 0 | 1 | 2 | 0 |
|  | 10 | 0 | 0 | 1 | 2* | 0 | 1 | 2 | 0 |
|  | 2.5 | 1* | 1 | 4 | 3* | 0 | 1 | 4 | 1 |
|  | 1.0 | 1 | 2* | 4 | 4 | 0 | 3* | 4 | 4 |
| 50 | 40 | 4 | 0 | 0 | 4 | 2 | 0 | 2 | 0 |
|  | 10 | 4 | 4 | 4 | 4 | 3 | 0 | 4 | 2 |
|  | 2.5 | 4 | 4 | 4 | 4 | 3 | 2 | 4 | 4 |
|  | 1.0 | 4 | 4 | 4 | 4 | 3 | 4 | 4 | 4 |
| 51 | 40 | 0 | 0 | — | 0 | 0 | 0 | 0 | 0 |
|  | 10 | 0 | 0 | — | 1* | 0 | 1 | 0 | 0 |
|  | 2.5 | 3 | 0 | — | 4 | 0 | 3 | 4 | 0 |
|  | 1.0 | 4 | 3 | — | 4 | 3 | 4 | 4 | 0 |
| 52 | 40 | 0 | 0 | — | 0 | 0 | 0 | 0 | 0 |
|  | 10 | 0 | 0 | — | 0 | 0 | 0 | 0 | 0 |
|  | 2.5 | 3* | 0 | — | 3* | 0 | 0 | 2 | 0 |
|  | 1.0 | 4 | 0 | — | 4 | 4 | 4 | 4 | 2 |
| 53 | 40 | 0 | 0 | — | 0 | 0 | 0 | 0 | 0 |
|  | 10 | 0 | 0 | — | 0 | 0 | 0 | 0 | 0 |
|  | 2.5 | 0 | 0 | — | 0 | 0 | 0 | 1 | 0 |
|  | 1.0 | 3 | 2 | — | 2 | 0 | 1 | 2 | 1 |
| 54 | 40 | 1* | 0 | 0 | 4 | 0 | 0 | 0 | 0 |
|  | 10 | 2 | 0 | 0 | 4 | 0 | 0 | 0 | 0 |
|  | 2.5 | 4 | 0 | 0 | 4 | 0 | 0 | 0 | 0 |
|  | 1.0 | 4 | 0 | 1* | 4 | 2 | 1* | 2 | 0 |
| 55 | 40 | 1* | 0 | 0 | 0 | 0 | 0 | 1* | 0 |
|  | 10 | 1* | 0 | 0 | 1* | 0 | 0 | 0 | 0 |
|  | 2.5 | 3 | 0 | 0 | 2* | 1 | 0 | 0 | 0 |
|  | 1.0 | 4 | 1* | 1* | 4 | 2 | 1* | 1* | 0 |
| 56 | 40 | 0 | 0 | — | 0 | 0 | 0 | 0 | 0 |
|  | 10 | 0 | 0 | — | 0 | 0 | 0 | 0 | 0 |
|  | 2.5 | 0 | 0 | — | 3* | 0 | 0 | 2 | 0 |
|  | 1.0 | 4 | 0 | — | 4 | 4 | 4 | 4 | 1 |
| 57 | 40 | 0 | 0 | 0 | 0 | 0 | 0 | 0 | 0 |
|  | 10 | 0 | 0 | 0 | 0 | 0 | 0 | 0 | 0 |
|  | 2.5 | 1* | 2* | 0 | 2* | 0 | 1* | 0 | 0 |
|  | 1.0 | 3 | 0 | 2* | 4 | 3 | 4 | 4 | 0 |
| 58 | 40 | 0 | 0 | 0 | 0 | 0 | 0 | 0 | 0 |
|  | 10 | 0 | 0 | 0 | 0 | 0 | 0 | 0 | 0 |
|  | 2.5 | 0 | 0 | 1* | 3* | 0 | 2* | 0 | 0 |
|  | 1.0 | 3 | 4 | 2* | 4 | 3 | 3* | 4 | 2* |
| 59 | 40 | 3* | 0 | 1* | 4 | 0 | 0 | 1* | 0 |
|  | 10 | 4 | 0 | 0 | 4 | 0 | 1* | 1* | 0 |
|  | 2.5 | 4 | 0 | 1* | 4 | 0 | 1 | 1* | 2 |
|  | 1.0 | 4 | 0 | 1* | 4 | 1* | 4 | 2* | 2 |
| 60 | 40 | 3* | 0 | 0 | 3* | 0 | 0 | 0 | 0 |
|  | 10 | 3* | 0 | 0 | 4 | 0 | 1* | 1* | 0 |
|  | 2.5 | 3* | 0 | 1* | 4 | 0 | 2* | 1* | 0 |
|  | 1.0 | 4 | 0 | 2* | 4 | 0 | 4 | 2* | 0 |
| 61 | 40 | 2 | 1 | — | 2 | 0 | 0 | 0 | 0 |
|  | 10 | 3 | 2 | — | 2 | 0 | 3 | 1 | 2 |
|  | 2.5 | 4 | 4 | — | 3 | 0 | 4 | 1 | 1 |
|  | 1.0 | 4 | 4 | — | 4 | 4 | 4 | 1 | 2 |
| Benomyl | 40 | 4* | 0 | 0 | 4 | 0 | 1 | 0 | 0 |
|  | 10 | 4* | 3* | 0 | 4 | 3* | 0 | 0 | 1* |
|  | 2.5 | 4* | 4* | 3* | 4 | 4* | 2 | 2 | 1 |
|  | 1.0 | 4* | 4* | 3 | 4 | 4* | 2 | 2 | 4 |

*Abortive Germ Tubes

TABLE II
RESULTS OF IN VITRO MYCELIAL GROWTH INHIBITION EVALUATION

| | | Percent Fungus Growth Inhibition | | | | | | | |
|---|---|---|---|---|---|---|---|---|---|
| CPD No. | Conc. ppm | AS | PS | SF | PO | PU | RS | HO | CC |
| 1 | 10 | 100 | 100 | 100 | 82 | 100 | 100 | 100 | — |

TABLE II-continued
RESULTS OF IN VITRO MYCELIAL GROWTH INHIBITION EVALUATION Percent Fungus Growth Inhibition

| CPD No. | Conc. ppm. | AS | PS | SF | PO | PU | RS | HO | CC |
|---|---|---|---|---|---|---|---|---|---|
| | 5 | 100 | 100 | 100 | 42 | 0 | 64 | 100 | — |
| | 2.5 | 100 | 85 | 100 | 27 | 0 | 100 | 100 | — |
| 2 | 40 | 100 | 100 | 100 | 100 | 100 | 78 | 100 | 100 |
| | 20 | 100 | 76 | 100 | 56 | 100 | 100 | 100 | 100 |
| | 10 | 100 | 65 | 67 | 26 | 42 | 42 | 64 | 58 |
| | 5 | 75 | 53 | 52 | 22 | 0 | 0 | 55 | 46 |
| 3 | 40 | 100 | 65 | 100 | 93 | 100 | 100 | 100 | 100 |
| | 20 | 100 | 65 | 94 | 41 | 100 | 56 | 100 | 100 |
| | 10 | 63 | 53 | 67 | 41 | 100 | 20 | 64 | 67 |
| | 5 | 19 | 35 | 27 | 19 | 20 | 0 | 55 | 58 |
| 4 | 40 | 17 | 8 | 0 | 19 | 0 | 0 | 33 | 45 |
| | 20 | 0 | 0 | 4 | 0 | 0 | 0 | 24 | 27 |
| | 10 | 13 | 0 | 0 | 0 | 20 | 0 | 0 | 9 |
| | 5 | 13 | 0 | 0 | 0 | 0 | 0 | 0 | 0 |
| 5 | 40 | 100 | 71 | 73 | 63 | 100 | 64 | 100 | 100 |
| | 20 | 100 | 6 | 67 | 48 | 76 | 38 | 73 | 100 |
| | 10 | 100 | 35 | 42 | 22 | 42 | 0 | 64 | 75 |
| | 5 | 100 | 18 | 27 | 4 | 0 | 0 | 50 | 50 |
| 6 | 40 | 21 | 13 | 67 | 19 | 22 | 20 | 48 | 45 |
| | 20 | 13 | 0 | 0 | 19 | 0 | 0 | 0 | 0 |
| | 10 | 0 | 0 | 67 | 0 | 0 | 0 | 0 | 0 |
| | 5 | 8 | 0 | 0 | 15 | 0 | 0 | 0 | 0 |
| 7 | 40 | 92 | 88 | 100 | 81 | 100 | 76 | 100 | 100 |
| | 20 | 75 | 69 | 100 | 77 | 80 | 53 | 100 | 100 |
| | 10 | 75 | 54 | 100 | 65 | 29 | 33 | 43 | 36 |
| | 5 | 54 | 42 | 54 | 19 | 11 | 7 | 48 | 9 |
| 8 | 40 | 86 | 31 | 60 | 74 | 100 | 42 | 81 | 100 |
| | 20 | 69 | 31 | 51 | 48 | 100 | 7 | 0 | 67 |
| | 10 | 41 | 41 | 0 | 0 | 100 | 0 | 33 | 58 |
| | 5 | 38 | 3 | 0 | 23 | 0 | 0 | 24 | 50 |
| 9 | 40 | 100 | 100 | 100 | 93 | 100 | 78 | 100 | 100 |
| | 20 | 100 | 53 | 100 | 70 | 71 | 69 | 86 | 92 |
| | 10 | 63 | 76 | 76 | 48 | 80 | 42 | 82 | 75 |
| | 5 | 31 | 65 | 58 | 22 | 0 | 13 | 50 | 54 |
| 10 | 40 | 92 | 75 | 100 | 77 | 64 | 100 | 100 | 100 |
| | 20 | 92 | 50 | 100 | 58 | 42 | 100 | 100 | 100 |
| | 10 | 79 | 33 | 33 | 19 | 24 | 13 | 52 | 45 |
| | 5 | 54 | 17 | 42 | 19 | 11 | 9 | 57 | 9 |
| 11 | 40 | 100 | 75 | 100 | 62 | 100 | 91 | 100 | 100 |
| | 20 | 100 | 83 | 100 | 54 | 82 | 76 | 100 | 100 |
| | 10 | 83 | 33 | 100 | 38 | 18 | 38 | 100 | 64 |
| | 5 | 63 | 17 | 100 | 15 | 0 | 0 | 62 | 27 |
| 12 | 40 | 100 | 100 | 100 | 85 | 100 | 100 | 100 | 100 |
| | 20 | 63 | 65 | 100 | 59 | 100 | 64 | 100 | 71 |
| | 10 | 31 | 59 | 82 | 30 | 100 | 58 | 59 | 58 |
| | 5 | 31 | 71 | 64 | 19 | 42 | 20 | 59 | 63 |
| 13 | 40 | 100 | 100 | 100 | 100 | 100 | 76 | 81 | 100 |
| | 20 | 86 | 72 | 100 | 74 | 89 | 69 | 76 | 100 |
| | 10 | 59 | 50 | 67 | 42 | 73 | 53 | 86 | 67 |
| | 5 | 45 | 38 | 51 | 44 | 31 | 24 | 71 | 58 |
| 14 | 40 | 100 | 100 | 100 | 100 | 100 | 91 | 100 | 100 |
| | 20 | 100 | 100 | 87 | 55 | 100 | 76 | 100 | 100 |
| | 10 | 79 | 100 | 64 | 26 | 53 | 56 | 71 | 50 |
| | 5 | 86 | 44 | 47 | 23 | 31 | 53 | 71 | 67 |
| 15 | 40 | 75 | 83 | 88 | 58 | 76 | 53 | 100 | 100 |
| | 20 | 66 | 42 | 83 | 50 | 80 | 38 | 95 | 82 |
| | 10 | 66 | 42 | 83 | 19 | 76 | 38 | 90 | 55 |
| | 5 | 54 | 0 | 92 | 12 | 47 | 13 | 57 | 9 |
| 16 | 40 | 50 | 41 | 67 | 41 | 56 | 69 | 82 | 75 |
| | 20 | 56 | 47 | 67 | 48 | 47 | 31 | 55 | 67 |
| | 10 | 50 | 47 | 67 | 48 | 11 | 31 | 55 | 54 |
| | 5 | 38 | 53 | 64 | 41 | 7 | 29 | 64 | 58 |
| 17 | 40 | 100 | 100 | 100 | 71 | 100 | 76 | 100 | 100 |
| | 20 | 93 | 100 | 96 | 29 | 100 | 76 | 100 | 100 |
| | 10 | 72 | 75 | 76 | 48 | 80 | 53 | 100 | 100 |
| | 5 | 79 | 50 | 62 | 29 | 42 | 40 | 100 | 100 |
| 18 | 40 | 84 | 75 | 100 | 48 | 100 | 87 | 100 | 100 |
| | 20 | 90 | 75 | 89 | 48 | 100 | 76 | 100 | 100 |
| | 10 | 90 | 50 | 64 | 32 | 60 | 56 | 86 | 100 |
| | 5 | 69 | 41 | 51 | 26 | 13 | 42 | 86 | 83 |
| 19 | 40 | 100 | 100 | 100 | 87 | 100 | 82 | 100 | 100 |
| | 20 | 90 | 81 | 100 | 68 | 100 | 69 | 100 | 100 |
| | 10 | 62 | 66 | 76 | 48 | 80 | 47 | 90 | 100 |
| | 5 | 62 | 50 | 64 | 39 | 20 | 29 | 100 | 100 |
| 20 | 40 | 83 | 69 | 87 | 74 | 100 | 78 | 100 | 100 |
| | 20 | 59 | 100 | 84 | 68 | 91 | 76 | 100 | 100 |
| | 10 | 59 | 66 | 73 | 74 | 91 | 58 | 100 | 100 |
| | 5 | 59 | 59 | 60 | 48 | 53 | 51 | 100 | 100 |
| 21 | 40 | 100 | 100 | 100 | 58 | 100 | 100 | 100 | 85 |
| | 20 | 75 | 58 | 100 | 50 | 100 | 87 | 100 | 69 |
| | 10 | 63 | 62 | 100 | 33 | 33 | 64 | 86 | 38 |
| | 5 | 75 | 33 | 100 | 33 | 27 | 53 | 64 | 38 |
| 22 | 40 | 100 | 100 | 100 | 63 | 100 | 100 | 100 | 92 |
| | 20 | 100 | 83 | 100 | 54 | 96 | 91 | 100 | 69 |
| | 10 | 88 | 67 | 100 | 33 | 64 | 62 | 100 | 46 |
| | 5 | 63 | 17 | 24 | 21 | 20 | 42 | 100 | 31 |
| 23 | 40 | 100 | 100 | 100 | 58 | 100 | 78 | 100 | 100 |
| | 20 | 100 | 100 | 100 | 46 | 71 | 73 | 100 | 81 |
| | 10 | 81 | 33 | 100 | 42 | 69 | 53 | 100 | 38 |
| | 5 | 63 | 17 | 82 | 21 | 62 | 20 | 100 | 27 |
| 24 | 40 | 100 | 100 | 100 | 100 | 100 | 100 | 100 | 100 |
| | 20 | 100 | 100 | 100 | 63 | 64 | 82 | 100 | 100 |
| | 10 | 88 | 83 | 100 | 42 | 47 | 64 | 100 | 65 |
| | 5 | 100 | 33 | 100 | 21 | 0 | 20 | 86 | 46 |
| 25 | 40 | 88 | 100 | 100 | 63 | 100 | 78 | 100 | 100 |
| | 20 | 81 | 100 | 100 | 54 | 100 | 80 | 100 | 77 |
| | 10 | 75 | 100 | 100 | 58 | 47 | 64 | 100 | 50 |
| | 5 | 69 | 50 | 82 | 33 | 0 | 20 | 79 | 27 |
| 26 | 40 | 100 | 42 | 100 | 100 | 100 | 76 | 100 | 77 |
| | 20 | 100 | 17 | 100 | 90 | 13 | 42 | 57 | 49 |
| | 10 | 80 | 33 | 66 | 48 | 0 | 53 | 57 | 49 |
| | 5 | 60 | 13 | 17 | 0 | 0 | 0 | 43 | 37 |
| 27 | 40 | 87 | 42 | 86 | 81 | 80 | 64 | 57 | 54 |
| | 20 | 80 | 13 | 28 | 0 | 0 | 24 | 43 | 49 |
| | 10 | 73 | 8 | 21 | 24 | 0 | 31 | 21 | 40 |
| | 5 | 47 | 13 | 0 | 24 | 0 | 0 | 0 | 31 |
| 28 | 40 | 70 | 13 | 62 | 90 | 100 | 47 | 64 | 60 |
| | 20 | 50 | 17 | 0 | 52 | 91 | 24 | 21 | 26 |
| | 10 | 47 | 17 | 28 | 24 | 80 | 47 | 29 | 26 |
| | 5 | 40 | 0 | 17 | 24 | 0 | 20 | 29 | 14 |
| 29 | 40 | 47 | 13 | 7 | 0 | 0 | 29 | 0 | 31 |
| | 20 | 37 | 0 | 0 | 0 | 0 | 0 | 14 | 14 |
| | 10 | 30 | 0 | 31 | 14 | 0 | 31 | 0 | 11 |
| | 5 | 47 | 0 | 28 | 19 | 0 | 0 | 0 | 14 |
| 30 | 40 | 90 | 100 | 97 | 90 | 100 | 80 | 100 | 100 |
| | 20 | 81 | 90 | 97 | 84 | 96 | 69 | 100 | 100 |
| | 10 | 67 | 81 | 87 | 71 | 71 | 62 | 100 | 100 |
| | 5 | 29 | 52 | 50 | 10 | 20 | 42 | 59 | 75 |
| 31 | 40 | 67 | 58 | 52 | 57 | 0 | 76 | 100 | 69 |
| | 20 | 48 | 58 | 72 | 62 | 0 | 73 | 57 | 60 |
| | 10 | 60 | 42 | 52 | 48 | 0 | 69 | 86 | 57 |
| | 5 | 48 | 42 | 55 | 33 | 0 | 53 | 57 | 54 |
| 32 | 40 | 92 | 100 | 100 | 89 | 100 | 73 | 100 | 100 |
| | 20 | 88 | 100 | 76 | 100 | 100 | 69 | 100 | 69 |
| | 10 | 58 | 100 | 79 | 78 | 73 | 42 | 63 | 46 |
| | 5 | 58 | 100 | 74 | 67 | 73 | 76 | 100 | 35 |
| 33 | 40 | 100 | 93 | 100 | 100 | 100 | 100 | 100 | 83 |
| | 20 | 100 | 53 | 94 | 100 | 96 | 64 | 100 | 61 |
| | 10 | 100 | 33 | 61 | 68 | 87 | 42 | 91 | 28 |
| | 5 | 100 | 3 | 44 | 53 | 69 | 31 | 83 | 11 |
| 34 | 40 | 100 | 100 | 100 | 100 | 100 | 100 | 100 | 86 |
| | 20 | 100 | 50 | 100 | 100 | 87 | 76 | 100 | 61 |
| | 10 | 100 | 43 | 72 | 65 | 64 | 64 | 74 | 28 |
| | 5 | 100 | 13 | 33 | 38 | 0 | 24 | 74 | 6 |
| 35 | 40 | 100 | 80 | 100 | 100 | 100 | 76 | 100 | 92 |
| | 20 | 100 | 60 | 69 | 100 | 100 | 44 | 89 | 23 |
| | 10 | 100 | 35 | 27 | 38 | 11 | 7 | 100 | 0 |
| | 5 | 90 | 30 | 8 | 23 | 0 | 0 | 83 | 0 |
| 36 | 40 | 100 | 90 | 100 | 100 | 100 | 87 | 100 | 62 |
| | 20 | 100 | 60 | 58 | 100 | 100 | 42 | 89 | 38 |
| | 10 | 90 | 45 | 62 | 69 | 42 | 4 | 78 | 8 |
| | 5 | 71 | 30 | 38 | 31 | 0 | 0 | 78 | 0 |
| 37 | 40 | 54 | 42 | 59 | 61 | 100 | 51 | 47 | 52 |
| | 20 | 50 | 26 | 56 | 61 | 20 | 31 | 60 | 35 |
| | 10 | 50 | 16 | 59 | 44 | 0 | 42 | 13 | 29 |
| | 5 | 46 | 26 | 30 | 44 | 100 | 11 | 27 | 23 |
| 38 | 40 | 90 | 35 | 8 | 46 | 0 | 33 | 100 | 26 |
| | 20 | 33 | 30 | 0 | 23 | 0 | 7 | 89 | 0 |
| | 10 | 48 | 20 | 0 | 15 | 0 | 0 | 39 | 0 |
| | 5 | 5 | 10 | 0 | 8 | 0 | 0 | 56 | 0 |
| 39 | 40 | 54 | 42 | 85 | 61 | 100 | 42 | 80 | 32 |
| | 20 | 42 | 68 | 63 | 61 | 100 | 31 | 100 | 23 |

TABLE II-continued
RESULTS OF IN VITRO MYCELIAL GROWTH INHIBITION EVALUATION Percent Fungus Growth Inhibition

| CPD No. | Conc. ppm. | AS | PS | SF | PO | PU | RS | HO | CC |
|---|---|---|---|---|---|---|---|---|---|
| | 10 | 33 | 79 | 48 | 61 | 24 | 31 | 87 | 16 |
| | 5 | 42 | 42 | 41 | 42 | 0 | 24 | 73 | 16 |
| 40 | 40 | 100 | 53 | 100 | 89 | 100 | 53 | 100 | 48 |
| | 20 | 92 | 26 | 89 | 42 | 100 | 24 | 87 | 32 |
| | 10 | 75 | 16 | 59 | 47 | 100 | 0 | 60 | 48 |
| | 5 | 54 | 5 | 4 | 33 | 0 | 0 | 40 | 0 |
| 41 | 40 | 100 | 68 | 100 | 93 | 100 | 64 | 60 | 65 |
| | 20 | 58 | 42 | 100 | 59 | 100 | 51 | 33 | 48 |
| | 10 | 58 | 16 | 78 | 56 | 100 | 0 | 60 | 32 |
| | 5 | 54 | 16 | 56 | 22 | 0 | 0 | 40 | 10 |
| 42 | 40 | 90 | 38 | 100 | 68 | 100 | 67 | 100 | 18 |
| | 20 | 52 | 13 | 56 | 32 | 100 | 31 | 100 | 14 |
| | 10 | 33 | 19 | 35 | 11 | 42 | 4 | 38 | 22 |
| | 5 | 24 | 31 | 24 | 7 | 0 | 0 | 23 | 14 |
| 43 | 40 | 100 | 0 | 22 | 24 | 0 | 24 | 91 | 17 |
| | 20 | 100 | 0 | 17 | 24 | 0 | 11 | 65 | 6 |
| | 10 | 100 | 0 | 0 | 18 | 0 | 0 | 70 | 0 |
| | 5 | 80 | 0 | 0 | 13 | 0 | 0 | 61 | 0 |
| 44 | 40 | 100 | 100 | 100 | 100 | 100 | 100 | 100 | 100 |
| | 20 | 100 | 100 | 100 | 93 | 100 | 96 | 100 | 92 |
| | 10 | 62 | 100 | 100 | 71 | 100 | 80 | 100 | 56 |
| | 5 | 52 | 100 | 76 | 54 | 100 | 82 | 100 | 36 |
| 45 | 40 | 54 | 31 | 59 | 11 | 100 | 42 | 100 | 0 |
| | 20 | 25 | 6 | 38 | 0 | 69 | 13 | 63 | 12 |
| | 10 | 0 | 0 | 3 | 0 | 42 | 0 | 0 | 0 |
| | 5 | 4 | 0 | 9 | 0 | 0 | 0 | 0 | 0 |
| 46 | 40 | 100 | 100 | 100 | 100 | 100 | 100 | 100 | 100 |
| | 20 | 100 | 90 | 81 | 100 | 87 | 64 | 100 | 46 |
| | 10 | 81 | 70 | 76 | 77 | 40 | 56 | 89 | 0 |
| | 5 | 71 | 35 | 19 | 38 | 0 | 27 | 67 | 0 |
| 47 | 40 | 88 | 100 | 100 | 89 | 100 | 78 | 100 | 77 |
| | 20 | 92 | 100 | 100 | 100 | 100 | 69 | 100 | 46 |
| | 10 | 92 | 50 | 82 | 78 | 100 | 47 | 88 | 38 |
| | 5 | 92 | 38 | 82 | 78 | 71 | 58 | 75 | 27 |
| 48 | 40 | 100 | 100 | 100 | 100 | 100 | 76 | 100 | 100 |
| | 20 | 100 | 100 | 94 | 100 | 100 | 64 | 100 | 50 |
| | 10 | 92 | 50 | 88 | 67 | 42 | 24 | 63 | 33 |
| | 5 | 88 | 38 | 82 | 56 | 78 | 64 | 100 | 29 |
| 49 | 40 | 100 | 67 | 100 | 74 | 100 | 64 | 100 | 64 |
| | 20 | 100 | 34 | 75 | 53 | 96 | 42 | 100 | 33 |
| | 10 | 100 | 7 | 33 | 38 | 87 | 24 | 100 | 17 |
| | 5 | 100 | 0 | 14 | 29 | 47 | 9 | 74 | 3 |
| 50 | 40 | 63 | 100 | 100 | 100 | 100 | 47 | 100 | 100 |
| | 20 | 54 | 63 | 94 | 11 | 47 | 13 | 100 | 73 |
| | 10 | 21 | 38 | 47 | 0 | 0 | 0 | 38 | 54 |
| | 5 | 33 | 25 | 59 | 11 | 20 | 42 | 75 | 58 |
| 51 | 40 | 90 | 100 | 100 | 100 | 100 | 100 | 100 | 100 |
| | 20 | 81 | 100 | 92 | 92 | 91 | 82 | 100 | 85 |
| | 10 | 75 | 85 | 92 | 77 | 31 | 56 | 100 | 26 |
| | 5 | 52 | 60 | 69 | 46 | 0 | 20 | 78 | 8 |
| 52 | 40 | 90 | 100 | 100 | 100 | 100 | 100 | 100 | 77 |
| | 20 | 90 | 100 | 100 | 100 | 100 | 64 | 100 | 88 |
| | 10 | 71 | 90 | 81 | 77 | 60 | 64 | 89 | 46 |
| | 5 | 52 | 80 | 65 | 58 | 4 | 33 | 100 | 15 |
| 53 | 40 | 100 | 100 | 100 | 67 | 100 | 76 | 100 | 65 |
| | 20 | 67 | 100 | 100 | 78 | 100 | 76 | 100 | 71 |
| | 10 | 42 | 68 | 89 | 75 | 82 | 53 | 100 | 61 |
| | 5 | 38 | 42 | 63 | 69 | 20 | 53 | 27 | 45 |
| 54 | 40 | 100 | 20 | 64 | 65 | 87 | 71 | 100 | 50 |
| | 20 | 100 | 20 | 53 | 56 | 71 | 42 | 73 | 33 |
| | 10 | 100 | 30 | 50 | 53 | 60 | 42 | 91 | 28 |
| | 5 | 70 | 27 | 49 | 50 | 42 | 38 | 43 | 14 |
| 55 | 40 | 100 | 20 | 61 | 53 | 47 | 53 | 100 | 28 |
| | 20 | 100 | 17 | 56 | 51 | 33 | 31 | 91 | 22 |
| | 10 | 100 | 13 | 50 | 59 | 64 | 56 | 100 | 11 |
| | 5 | 100 | 0 | 42 | 41 | 42 | 33 | 100 | 0 |
| 56 | 40 | 100 | 100 | 100 | 100 | 100 | 100 | 100 | 100 |
| | 20 | 81 | 100 | 100 | 100 | 100 | 100 | 100 | 100 |
| | 10 | 71 | 100 | 78 | 67 | 67 | 78 | 100 | 38 |
| | 5 | 52 | 70 | 69 | 38 | 0 | 33 | 67 | 26 |
| 57 | 40 | 90 | 100 | 100 | 61 | 100 | 78 | 100 | 78 |
| | 20 | 90 | 100 | 100 | 71 | 100 | 80 | 100 | 78 |
| | 10 | 90 | 100 | 82 | 61 | 60 | 69 | 100 | 56 |
| | 5 | 71 | 88 | 68 | 46 | 42 | 53 | 100 | 42 |
| 58 | 40 | 43 | 44 | 71 | 50 | 13 | 64 | 69 | 61 |
| | 20 | 43 | 56 | 68 | 29 | 0 | 53 | 69 | 42 |
| | 10 | 48 | 56 | 65 | 54 | 24 | 58 | 54 | 44 |
| | 5 | 48 | 56 | 56 | 43 | 13 | 56 | 54 | 44 |
| 59 | 40 | 57 | 56 | 74 | 50 | 29 | 69 | 100 | 61 |
| | 20 | 57 | 69 | 59 | 50 | 0 | 33 | 100 | 47 |
| | 10 | 52 | 56 | 68 | 61 | 0 | 24 | 100 | 42 |
| | 5 | 48 | 50 | 71 | 50 | 0 | 33 | 100 | 28 |
| 60 | 40 | 52 | 75 | 71 | 64 | 13 | 56 | 100 | 47 |
| | 20 | 52 | 56 | 65 | 43 | 0 | 42 | 69 | 44 |
| | 10 | 43 | 50 | 71 | 43 | 0 | 31 | 77 | 36 |
| | 5 | 33 | 63 | 56 | 32 | 9 | 42 | 100 | 33 |
| 61 | 40 | 42 | 0 | 85 | 44 | 100 | 47 | 100 | 52 |
| | 20 | 25 | 23 | 59 | 50 | 100 | 33 | 100 | 32 |
| | 10 | 29 | 46 | 19 | 42 | 42 | 13 | 33 | 23 |
| | 5 | 33 | 16 | 7 | 28 | 31 | 0 | 13 | 6 |
| Captan | 40 | — | 44 | — | — | 0 | 0 | 65 | — |
| | 20 | — | 48 | — | — | 0 | 0 | 62 | — |
| | 10 | — | 33 | — | — | 0 | 0 | 46 | — |
| | 5 | — | 19 | — | — | 0 | 0 | 18 | — |
| Chlorothalonil | 40 | 75 | 88 | 82 | 48 | 100 | 73 | 95 | 96 |
| | 20 | 38 | 76 | 76 | 41 | 100 | 53 | 73 | 71 |
| | 10 | 50 | 41 | 70 | 15 | 31 | 40 | 59 | 63 |
| | 5 | 44 | 41 | 67 | 26 | 0 | 31 | 50 | 63 |

TABLE III
RESULTS OF PLANT TESTS

| | Percent Disease Control | | | | | | | Efficacy Index |
|---|---|---|---|---|---|---|---|---|
| | Foliar | | | Curative | | | Seed/Soil | |
| CPD No. | Tomato Late Blight | Bean Rust | Bean Rust | Bean Powdery Mildew | Sugar Beet Leaf Spot | Rice Blast | Bean Root Rot | Cucumber Damping-off Complex |
|---|---|---|---|---|---|---|---|---|
| 1 | 0 | 0 | 0 | 0 | 0 | 0 | 0 | 0 |
| 2 | 0 | 100 | 0 | 100 | 0 | 0 | 100 | 89 |
| 3 | 50 | 100 | 0 | 0 | 0 | 0 | 80 | 88 |
| 4 | 0 | 100 | 75 | 100 | 0 | 95 | 0 | 44 |
| 5 | 0 | 100 | 0 | 0 | 0 | 75 | 50 | 0 |
| 6 | 0 | 0 | 90[c] | 100 | 0 | 0 | 0 | 33 |
| 7 | 100 | 100 | 0 | 0 | 75 | 0 | 98 | 33 |
| 8 | 90 | 100[b] | 0 | 0 | 0 | 0 | 0 | 0 |
| 9 | 90 | 98 | 0 | 0 | 75 | 90 | 0 | 76 |
| 10 | 100 | 100 | 0 | 0 | 95 | 0 | 0 | 122 |
| 11 | 100 | 0 | 0 | 100 | 0 | 0 | 0 | 100 |
| 12 | 100 | 100 | 0 | 50 | 95 | 75 | 0 | 71 |
| 13 | 98 | 100[b] | 90[b] | 100 | 98 | 0 | 75 | 0 |

TABLE III-continued
RESULTS OF PLANT TESTS

| | Percent Disease Control | | | | | | | Efficacy Index |
|---|---|---|---|---|---|---|---|---|
| | Foliar | | Curative | | | | Seed/Soil | |
| CPD No. | Tomato Late Blight | Bean Rust | Bean Rust | Bean Powdery Mildew | Sugar Beet Leaf Spot | Rice Blast | Bean Root Rot | Cucumber Damping-off Complex |
| 14 | 0 | 0 | 100 | 50 | 0 | 0 | 90 | 76 |
| 15 | 100 | 100 | 90[c] | 100 | 0 | 95 | 0 | 133 |
| 16 | 0 | 90 | 0 | 0 | 95 | 90 | 0 | 0 |
| 17 | 100 | 100 | 100 | 100 | 95 | 0 | 0 | 0 |
| 18 | 50 | 100 | 0 | 100 | 98 | 0 | DP[a] | 0 |
| 19 | 0 | 0 | 100 | DP[a] | 0 | 0 | 0 | 0 |
| 20 | 0 | 100 | 0 | 100[b] | 95 | 0 | 75 | 0 |
| 21 | 50 | 100 | 0 | 100 | 100 | 85 | 0 | 77 |
| 22 | 0 | 100 | 0 | 100 | 0 | 0 | 0 | 100 |
| 23 | 0 | 100 | 0 | 0 | 100 | 0 | 0 | 94 |
| 24 | 98 | 100 | 0 | 100 | 50 | 95 | 0 | 100 |
| 25 | 100 | 100 | 0 | 100 | 50 | 0 | 0 | 105 |
| 26 | 0[c] | 0 | 0 | 0 | 95 | 0 | 0 | 0 |
| 27 | 98 | 0 | 0 | 0 | 95 | 95 | 0 | 83 |
| 28 | 90 | 0 | 0 | 50 | 0 | 0 | 95 | 0 |
| 29 | 100 | 0 | 0 | 0 | 95 | 0 | 0 | 94 |
| 30 | 0 | 100 | 0 | 100 | 0 | 0 | 0 | 0 |
| 31 | 0 | 0 | 0 | 100 | 0 | 0 | 0 | 0 |
| 32 | 0 | 90 | 0 | 90 | 90 | 0 | 0 | 95 |
| 33 | 0 | 100 | 0 | 95 | 0 | 0 | 95 | 0 |
| 34 | 0 | 85 | 0 | 95 | 0 | 0 | 0 | 0 |
| 35 | 100 | 100 | 0 | 0 | — | 0 | — | — |
| 36 | 90 | 100 | 0 | 0 | — | 95 | — | 13 |
| 37 | 0 | 100 | 0 | 0 | — | 0 | — | — |
| 38 | 0 | 0 | 100 | 0 | — | 0 | — | — |
| 39 | 0 | 98 | 0 | 0 | — | 0 | — | — |
| 40 | 75 | 98 | 0 | 0 | — | 0 | — | — |
| 41 | 90 | 0 | 0 | 0 | — | 0 | — | — |
| 42 | 0 | 100 | 0 | 0 | 0 | 0 | 90 | 111 |
| 43 | 0 | 0 | 0 | 0 | 90 | 0 | 0 | 90 |
| 44 | 0 | 100 | 0 | 100 | 0 | 0 | 90 | 111 |
| 45 | 0 | 95 | 0 | 0 | 90 | 0 | 90 | 65 |
| 46 | 75 | 0 | 0 | 0 | — | 0 | — | — |
| 47 | 95 | 0 | 0 | 0 | 90 | 90 | 95 | 105 |
| 48 | 98 | 100 | 0 | 0 | DP[a] | 50 | 95 | 80 |
| 49 | 90 | 100 | 0 | 0 | 0 | 0 | 0 | 100 |
| 50 | 0 | 90 | 0 | 0 | 50 | 90 | 0 | 0 |
| 51 | 90 | 0 | 0 | 0 | — | 0 | — | — |
| 52 | 50 | 0 | 0 | 75 | — | 95 | — | — |
| 53 | 98 | 100 | 0 | 0 | — | 0 | — | — |
| 54 | 0 | 100 | 0 | 0 | 0 | 0 | 0 | 0 |
| 55 | 90 | 100[b] | 0 | 50 | 95 | 50 | 0 | 0 |
| 56 | 95 | 0 | 100 | 0 | — | 0 | — | — |
| 57 | 0 | 100 | 0 | 100 | 90 | 0 | 0 | 0 |
| 58 | 0 | 100 | 0 | 50 | 0 | 0 | 0 | 0 |
| 59 | 0 | 0 | 0 | DP[a] | 0 | 0 | 0 | 0 |
| 60 | 0 | 100 | 0 | DP[a] | 0 | 0 | 0 | 0 |
| 61 | 0 | 100 | 0 | 0 | — | 0 | — | — |

[a]DP = Dead Plant
[b]Slight Phytotoxicity
[c]Marginal Disease

We claim:
1. A compound of the formula

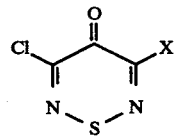

in which X is naphthoxy or substituted phenoxy having the formula

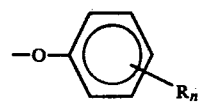

wherein each R group is a substituent independently selected from the group consisting of lower alkyl, halo, hydroxy, lower alkoxy, nitro, cyano, amino, carboxyl, lower acyl, lower acylamino, lower alkoxycarbonyl, carboxy(lower)alkyl, lower alkylureido, phenylureido, trihalomethyl, cyano(lower)alkyl, phenyl(lower)alkoxycarbonyloxy, lower alkylaminocarbonyloxy, phenylaminocarbonyloxy, lower alkylthio, lower alkylsulfinyl and lower alkylsulfonyl, wherein n has a value of 1 to 3 inclusive, except when each R is halogen when n has a value of 1 to 5 inclusive.

2. The compound of claim 1 in which R is independently selected from the group consisting of lower alkyl and halo.

3. The compound of claim 2 in which each R is halogen.

4. The compound of claim 3 in which each R is chlorine.

5. The compound of claim 2 in which each R is lower alkyl.

6. The compound of claim 5 in which each R is methyl.

* * * * *

UNITED STATES PATENT AND TRADEMARK OFFICE
CERTIFICATE OF CORRECTION

PATENT NO. : 4,450,269
DATED : May 22, 1984
INVENTOR(S) : Clinton J. Peake; Wayne N. Harnish; Bruce L. Davidson It is certified that error appears in the above—identified patent and that said Letters Patent is hereby corrected as shown below:

Column 1, line 19, "angifungal" should read --antifungal--.
Column 4, line 31, "3,5-dichloro4H-1,2,6-thiadiazin-4-one" should read --3,5-dichloro-4H-1,2,6-thiadiazin-4-one--; Example II, Table, Compound 4, "3-chloro-5-(4-tert-butyl-phnoxy)-4H-1,2,6-thiadiazin-4-one" should read --3-chloro-5-(4-tert-butyl-phenoxy)-4H-1,2,6-thiadiazin-4-one--.
Column 5, Example II, Table, Compound 27, "5-(4-aminophenoxy)-3-chloro-4H-1,2,6-thiadiazine-4-one hydrochloride" should read --5-(4-aminophenoxy)-3-chloro-4H-1,2,6-thiadiazin-4-one hydrochloride--; Example II, Table, Compound 31, "3-chloro-5-(pentachlorophenoxy)-4H-1,2,6-thiadiazine-4-one" should read --3-chloro-5-(pentachlorophenoxy)-4H-1,2,6-thiadiazin-4-one--; Example II, Table, Compound 32, "3-chloro-5(1-naphthoxy)-4H-1,2,6-thiadiazin-4-one" should read --3-chloro-5-(1-naphthoxy)-4H-1,2,6-thiadiazin-4-one--; Example II, Table, Compound 38, "3-chloro-5-[4-(phenyl methoxycarbonyloxy)phenoxyl]-4H-1,2,6-thiadiazin-4-one"

UNITED STATES PATENT AND TRADEMARK OFFICE
CERTIFICATE OF CORRECTION

PATENT NO. : 4,450,269

DATED : May 22, 1984

INVENTOR(S) : Clinton J. Peake; Wayne N. Harnish; Bruce L. Davidson

It is certified that error appears in the above—identified patent and that said Letters Patent is hereby corrected as shown below:

should read --3-chloro-5-[4-(phenyl methoxycarbonyloxy)-phenoxy]-4H-1,2,6-thiadiazin-4-one--. Column 6, Example II, Footnote to Table, "PS = Fusarium solani" should read --FS = Fusarium solani--. Column 7, line 37, "72" should read --72-144--, Column 9, line 4, "[Straight" should read --'Straight--. Column 12, Table II, Heading "PS" should read --FS--. Column 13, Table II, Heading "PS" should read --FS--. Column 14, Table II, Heading "PS" should read --FS--. Column 15, Table II, Heading "PS" should read --FS--. Column 16, Table II, Heading "PS" should read --FS--. Column 17, Table III, Compound 26, "O$^C$" should read --O$^B$--; Table III, Compound 36, "13" should read -- - --, Signed and Sealed this Ninth Day of April 1985

[SEAL]

Attest:

DONALD J. QUIGG

Attesting Officer     Acting Commissioner of Patents and Trademarks